United States Patent
Komoro (10) Patent No.: US 11,903,566 B2
(45) Date of Patent: Feb. 20, 2024

(54) IMAGING MODULE AND ENDOSCOPE HAVING IMAGE SENSOR AND MOUNTING BOARD

(71) Applicant: HOYA CORPORATION, Tokyo (JP)

(72) Inventor: Atsushi Komoro, Tokyo (JP)

(73) Assignee: HOYA CORPORATION, Tokyo (JP)

(*) Notice: Subject to any disclaimer, the term of this patent is extended or adjusted under 35 U.S.C. 154(b) by 59 days.

(21) Appl. No.: 17/259,735

(22) PCT Filed: Mar. 12, 2020

(86) PCT No.: PCT/JP2020/010707
§ 371 (c)(1),
(2) Date: Jan. 12, 2021

(87) PCT Pub. No.: WO2020/195872
PCT Pub. Date: Oct. 1, 2020

(65) Prior Publication Data
US 2022/0000352 A1 Jan. 6, 2022

(30) Foreign Application Priority Data
Mar. 27, 2019 (JP) ................... 2019-061430

(51) Int. Cl.
*A61B 1/05* (2006.01)
*A61B 1/00* (2006.01)
(Continued)

(52) U.S. Cl.
CPC .......... *A61B 1/051* (2013.01); *A61B 1/00124* (2013.01); *H04N 23/54* (2023.01); *H04N 23/555* (2023.01)

(58) Field of Classification Search
CPC ..... A61B 1/051; A61B 1/00124; A61B 1/053; A61B 1/05; H04N 23/54; H04N 23/555; H04N 23/57; G02B 23/2484
(Continued)

(56) References Cited

U.S. PATENT DOCUMENTS 7,914,442 B1 * 3/2011 Gazdzinski ........ A61B 1/00156
600/128
9,345,395 B2 * 5/2016 Takahashi .............. H04N 25/70
(Continued)

FOREIGN PATENT DOCUMENTS

JP        8-146310 A     6/1996
JP       2006-25852 A    2/2006
(Continued)

OTHER PUBLICATIONS

International Search Report (ISR) dated May 26, 2020 filed in PCT/JP2020/010707.

*Primary Examiner* — John P Leubecker
*Assistant Examiner* — Li-Ting Song
(74) *Attorney, Agent, or Firm* — GREENBLUM & BERNSTEIN, P.L.C.

(57) ABSTRACT

An imaging module includes: an image sensor; and a mounting board on which the image sensor is mounted together with a plurality of passive components. The mounting board includes: a first surface on which the image sensor is surface-mounted; a second surface that is located on an opposite side to the first surface and on which the passive component is mounted; a third surface that is continuous with the second surface via a step and on which the passive component is mounted; and a columnar cable connection block that rises from the second and third surfaces and to which a cable is connected.

7 Claims, 6 Drawing Sheets

(51) Int. Cl.
*H04N 23/54* (2023.01)
*H04N 23/50* (2023.01)

(58) Field of Classification Search
USPC .......................................................... 600/109
See application file for complete search history.

(56) References Cited

U.S. PATENT DOCUMENTS

| | | | |
|---|---|---|---|
| 9,455,358 B2* | 9/2016 | Nakayama | H01L 27/14618 |
| 11,249,300 B1* | 2/2022 | Lin | H04N 23/56 |
| 2004/0171914 A1* | 9/2004 | Avni | H05K 3/3436 |
| | | | 600/109 |
| 2012/0206583 A1* | 8/2012 | Hoshi | A61B 1/042 |
| | | | 348/76 |
| 2014/0179999 A1* | 6/2014 | Igarashi | A61B 1/0661 |
| | | | 600/109 |
| 2015/0359420 A1* | 12/2015 | Hatase | A61B 1/0055 |
| | | | 600/110 |
| 2016/0205296 A1* | 7/2016 | Igarashi | A61B 1/0008 |
| | | | 348/76 |
| 2017/0127921 A1* | 5/2017 | Motohara | H04N 23/57 |
| 2017/0255001 A1 | 9/2017 | Yamashita et al. | |
| 2018/0070805 A1* | 3/2018 | Kawayoke | H04N 23/54 |
| 2019/0069767 A1* | 3/2019 | Mikami | A61B 1/00114 |
| 2019/0214426 A1 | 7/2019 | Shimohata et al. | |
| 2019/0216304 A1* | 7/2019 | Kimura | A61B 1/00124 |
| 2019/0343375 A1* | 11/2019 | Sato | A61B 1/051 |
| 2020/0337538 A1* | 10/2020 | Ishikawa | A61B 1/00124 |
| 2020/0367734 A1* | 11/2020 | Shimizu | A61B 1/00124 |
| 2021/0096355 A1* | 4/2021 | Nishimura | G02B 23/26 |
| 2023/0291988 A1* | 9/2023 | Ishikawa | A61B 1/05 |
| | | | 348/75 |

FOREIGN PATENT DOCUMENTS

| | | |
|---|---|---|
| JP | 2008-177298 A | 7/2008 |
| JP | 2015-173736 A | 10/2015 |
| JP | 2016-36558 A | 3/2016 |
| WO | 2018/078766 A1 | 5/2018 |

* cited by examiner

IMAGING MODULE AND ENDOSCOPE HAVING IMAGE SENSOR AND MOUNTING BOARD

TECHNICAL FIELD

The present invention relates to an imaging module and an endoscope including an imaging module.

BACKGROUND ART

An endoscope is medical equipment that is inserted into a body cavity of a subject to enable observation and treatment of a desired location, and includes an imaging module incorporated in a distal tip of an insertion tube inserted into the body cavity. The imaging module includes an image sensor such as a complementary metal oxide semiconductor (CMOS) and a mounting board on which the image sensor is mounted together with a plurality of passive components.

In the endoscope, in order to reduce the burden on the subject, a diameter of the insertion tube is being reduced, and there is a need to downsize the imaging module incorporated in the distal tip of the insertion tube, and more specifically, reduce a projected area in a cross section perpendicular to an axis. Patent Literatures 1 and 2 disclose a downsized imaging module.

CITATION LIST

Patent Literature

Patent Literature 1: JP 2015-173736 A
Patent Literature 2: JP 2016-36558 A

SUMMARY OF INVENTION

Technical Problem

The imaging module disclosed in Patent Literature 1 includes an element board that has an image sensor surface-mounted on one surface thereof, and a bottomed cylindrical cable connection board that is fixedly layered on the other surface of the element board and has a cable connection part on an outer peripheral surface thereof and a mounting part of a passive component on a bottom surface thereof, in which the projected area is reduced by the stack of the element board and the cable connection board. In this configuration, when it is necessary to implement the plurality of passive components, the projected area of the cable connection board having the mounting part on the bottom thereof becomes large, and it is difficult to meet the demand for miniaturization of the imaging module.

The imaging module disclosed in Patent Literature 2 includes a circuit board that has a device mounting surface on which an image sensor is surface-mounted and a component mounting surface of a passive component orthogonal to the element mounting surface, in which it is possible to mount the plurality of passive components by extending the component mounting surface in the axial direction. In this configuration, the demand for reduction of the projected area can be met, but the axial dimension of the imaging module increases, which may affect the operation of changing the direction of the distal tip of the insertion tube in which the imaging module is incorporated.

An object of the present disclosure is to provide an imaging module capable of meeting miniaturization demands and an endoscope provided with this imaging module.

Solution to Problem

An imaging module according to the present disclosure includes: an image sensor; and a mounting board on which the image sensor is mounted together with a plurality of passive components, in which a mounting part of the image sensor and a mounting part of the passive component are located on opposite sides of the mounting board, and the mounting part of the passive component is provided with a plurality of mounting surfaces that are continuous with each other via a step and are each provided with a connection land of the passive component.

An imaging module according to the present disclosure includes: an image sensor; and a mounting board on which the image sensor is mounted together with a plurality of passive components, in which the mounting board includes: a first surface on which the image sensor is surface-mounted; a second surface that is located on an opposite side to the first surface and is provided with a connection land of the passive component; a third surface that is continuous with the second surface via a step and is provided with the connection land of the passive component; and a columnar cable connection block that rises from the second and third surfaces and to which a cable is connected.

Further, the mounting board further includes a fourth surface which is continuous with the second and third surfaces via a step and is provided with the connection land of the passive component.

Further, cable connection lands for connecting a plurality of core wires of the cable are arranged side by side on the side surface of the cable connection block.

Further, the cable is a shielded cable, and a grounding land for grounding the shield is provided on an end surface of the cable connection block.

Further, the mounting board has a projected area equal to or smaller than that of the image sensor in a cross section perpendicular to an axis.

An endoscope according to the present disclosure includes an imaging module incorporated in a distal tip of an insertion tube, in which the imaging module includes: an image sensor; and a mounting board on which the image sensor is mounted together with a plurality of passive components, and the mounting board includes: a first surface on which the image sensor is surface-mounted; a second surface that is located on an opposite side to the first surface and is provided with a connection land of the passive component; a third surface that is continuous with the second surface via a step and is provided with the connection land of the passive component; and a columnar cable connection block that rises from the second and third surfaces and to which a cable is connected.

Advantageous Effects of Invention

According to the present disclosure, it is possible to provide the imaging module that can meet the demand for miniaturization by reducing the projected area in the cross section perpendicular to the axis by suppressing the increase in the axial dimension and the endoscope in which the imaging module is incorporated.

DESCRIPTION OF EMBODIMENTS

Hereinafter, embodiments of the present disclosure will be described with reference to the drawings.

First Embodiment

Figure 1:
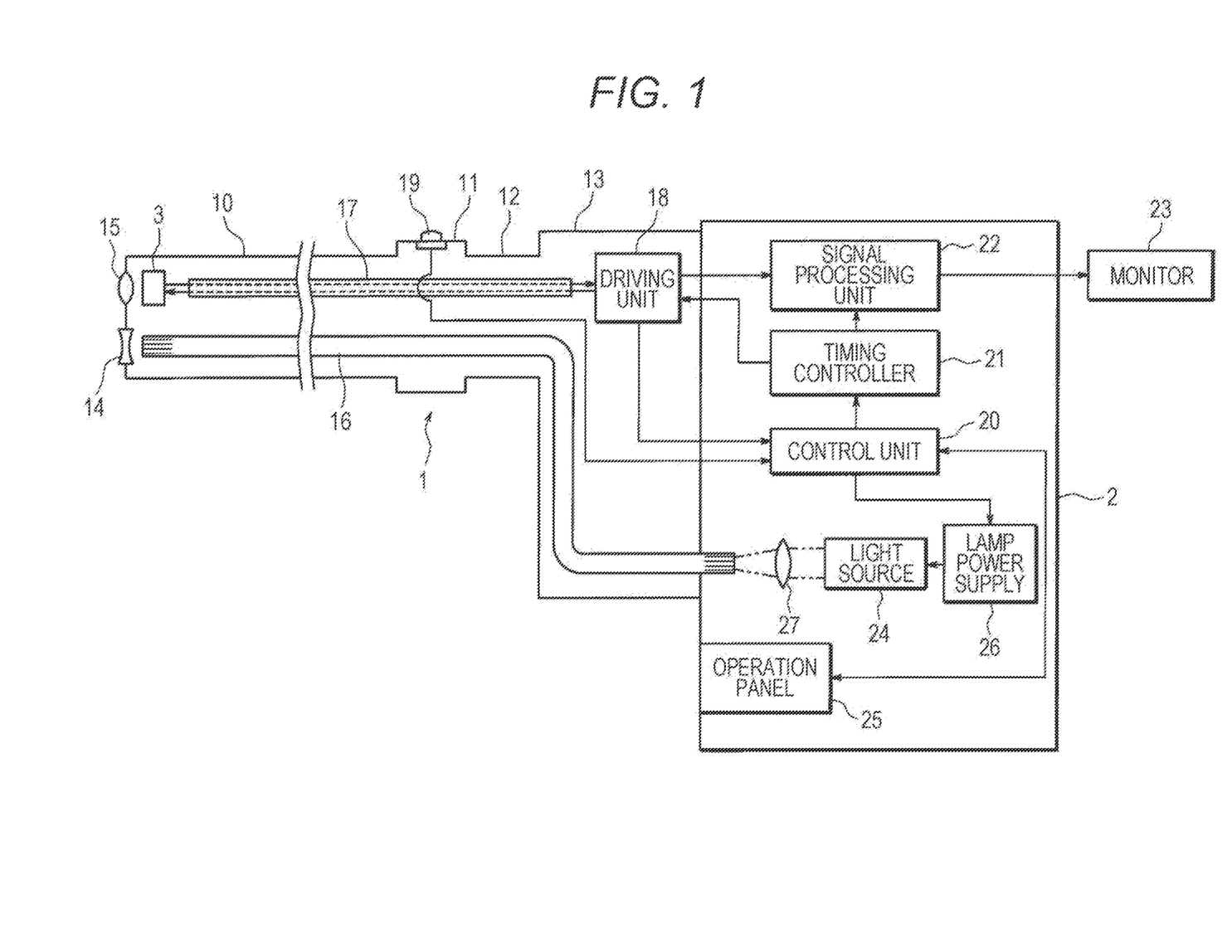
FIG. 1 is a block diagram of an endoscope device.

FIG. 1 is a block diagram of an endoscope device. The endoscope device includes an endoscope 1 and a processor device 2. The endoscope 1 includes an insertion tube 10 that is inserted into a body cavity of a subject, and a connector unit 13 that is connected to the insertion tube 10 via an operation unit 11 and a universal tube 12, and is used by being connected to the processor device 2 by the connector unit 13.

A light distribution lens 14 and an objective lens 15 are attached to a distal tip of the insertion tube 10. One end of a light guide 16 faces an inner side of the light distribution lens 14, and an imaging module 3 having a configuration described later is incorporated inside the objective lens 15, with an imaging surface facing the objective lens 15.

The light guide 16 is configured by bundling a plurality of optical fibers, and extends to the connector unit 13 through the inside of the insertion tube 10, the operation unit 11, and the universal tube 12. The imaging module 3 is connected to a driving unit 18 that is provided in the connector unit 13 by a cable 17 passing through the inside of the insertion tube 10, the operation unit 11, and the universal tube 12. The cable 17 is a shielded cable including a plurality of core wires such as a control line and a signal line.

The operation unit 11 is provided with operation buttons for performing various operations. FIG. 1 illustrates a control button 19. The control button 19 is provided for remote control of the processor device 2 connected by the connector unit 13.

The processor device 2 includes a control unit 20, a timing controller 21, and a signal processing circuit 22. The control unit 20 includes a CPU, a ROM, and a RAM, and performs integrated control on the endoscope device by operating the CPU according to a control program stored in the ROM. The control unit 20 is connected to the driving unit 18 provided in the connector unit 13 of the endoscope 1 and the control button 19 provided in the operation unit 11. The driving unit 18 outputs unique information (number of pixels, sensitivity, field rate, and the like) of the imaging module 3 to the control unit 20. The control unit 20 operates in response to the operation of the control button 19, performs various calculations based on the unique information given from the driving unit 18, and outputs a control command to each unit.

The timing controller 21 generates a clock pulse according to the control command given from the control unit 20, and outputs the generated clock pulse to the signal processing circuit 22 and the driving unit 18 provided in the connector unit 13. The driving unit 18 drives the imaging module 3 at a timing synchronized with the clock pulse output from the timing controller 21. The imaging module 3 outputs an image signal by an imaging operation to be described later.

The image signal output by the imaging module 3 is preprocessed in the driving unit 18 and input to the signal processing circuit 22 of the processor device 2 in a one field cycle. The clock pulse is input to the signal processing circuit 22 from the timing controller 21, and the signal processing circuit 22 performs image processing, such as gamma correction and interpolation processing, on the input image signal, superimposition processing on various characters and images, and the like according to the clock pulse, and converts the processed images into an image signal conforming to a predetermined standard, and then outputs the converted processed images to the external monitor 23. The monitor 23 is a display device such as a liquid crystal display and an organic EL display, and displays an image captured by the imaging module 3 based on the image signal output from the processor device 2.

The processor device 2 further includes a light source 24 and an operation panel 25. The light source 24 is a high intensity lamp such as a xenon lamp, a halogen lamp, or a metal halide lamp, and is lit up by power from a lamp power supply 26. The lamp power supply 26 includes an igniter for lighting the light source 24, a stabilized power supply device for controlling current after the lighting, and the like, and lights and lights-out the light source 24 according to a control command given from the control unit 20.

An end of the light guide 16 of the endoscope 1 is inserted into the processor device 2 by the connection of the connector unit 13 and faces the light source 24 via a condenser lens 27. The light emitted from the light source 24 is condensed by the condenser lens 27 and introduced into the light guide 16 as illustrated by a two-dot chain line in FIG. 1. The light introduced into the light guide 16 is guided to the distal tip of the insertion tube 10, diffused by the light distribution lens 14 to be emitted, and illuminates the inside of the body cavity into which the insertion tube 10 is inserted.

The imaging module 3 images the inside of the body cavity under illumination, and the captured image is subjected to the image processing by the signal processing circuit 22 and displayed on the monitor 23 as a moving image or a still image. A user of the endoscope 1 can observe a desired position in the body cavity from the display image of the monitor 23 by changing the insertion position of the insertion tube 10 and further changing the direction of the distal tip at an appropriate insertion position. The imaging by the imaging module 3 is executed in response to the operation of the control button 19 provided on the operation unit 11. Further, the direction of the distal tip of the insertion tube 10 is changed by operating an operation knob (not illustrated) provided on the operation unit 11.

The operation panel 25 includes an operation button and a touch panel type graphical user interface (GUI), and is operatively equipped in the housing of the processor device 2 from the outside. The operation panel 25 is connected to the control unit 20, and various settings including imaging conditions such as brightness and contrast can be made by operating the operation panel 25.

Figure 2:
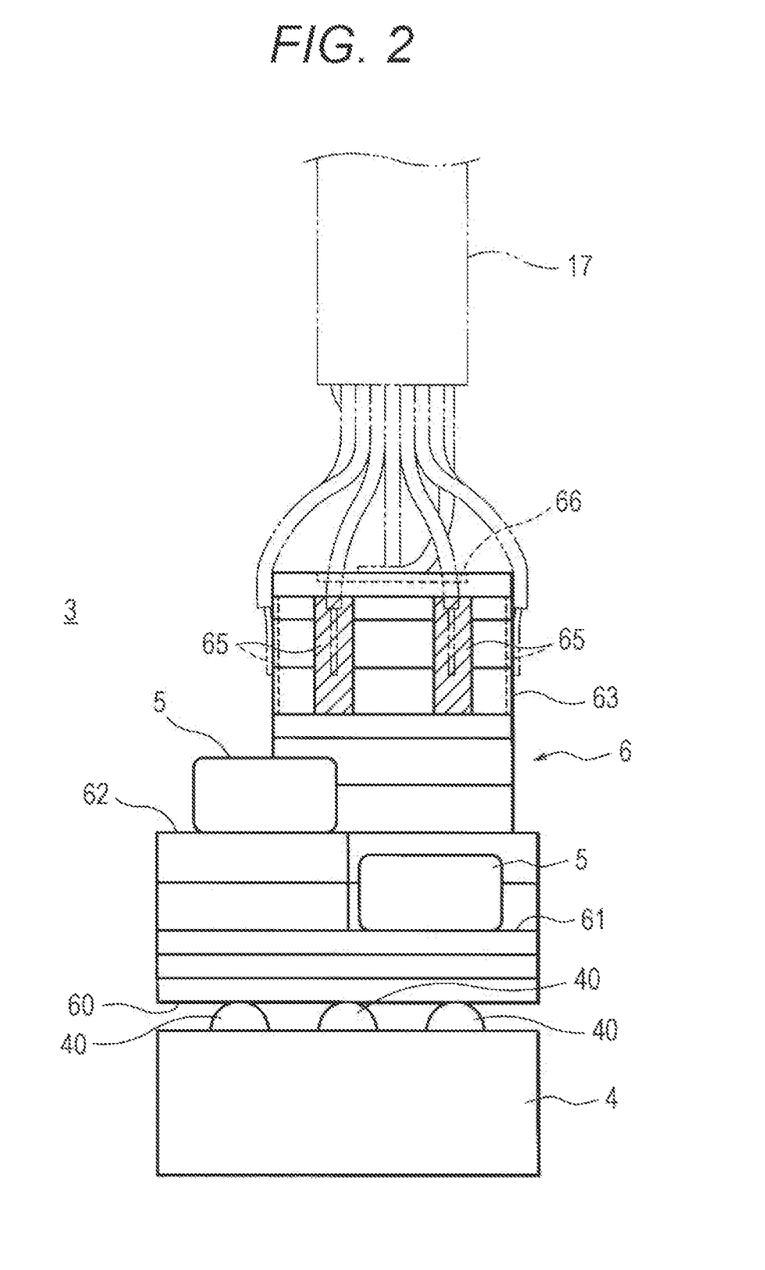
FIG. 2 is a side view of an imaging module according to a first embodiment.

FIG. 2 is a side view of an imaging module 3 according to a first embodiment. The imaging module 3 illustrated includes an image sensor 4, three passive components 5, and a mounting board 6 on which the image sensor 4 and the passive components 5 are mounted.

The image sensor 4 is, for example, a complementary metal oxide semiconductor (CMOS), a charge coupled device (CCD), or the like, and converts an optical image joined to a rectangular imaging surface (lower surface in the figure) into an electric signal and outputs the electric signal. A plurality of electrodes 40 for input and output are vertically and horizontally provided on a back surface (surface opposite to the imaging surface) of the image sensor 4, and the image sensor 4 is surface-mounted on a first surface 60 of the mounting board 6 by these electrodes 40.

The passive component 5 is an electronic component, which processes the output signal of the image sensor 4 and converts the processed output signal into an image signal indicating luminance of each pixel of the image sensor 4 and outputs the image signal, such as a capacitor or the like that bypasses between a power supply line and a ground, and is mounted on a second surface 61 and a third surface 62 provided on an opposite side of the first surface 60 as described later.

Figure 3:
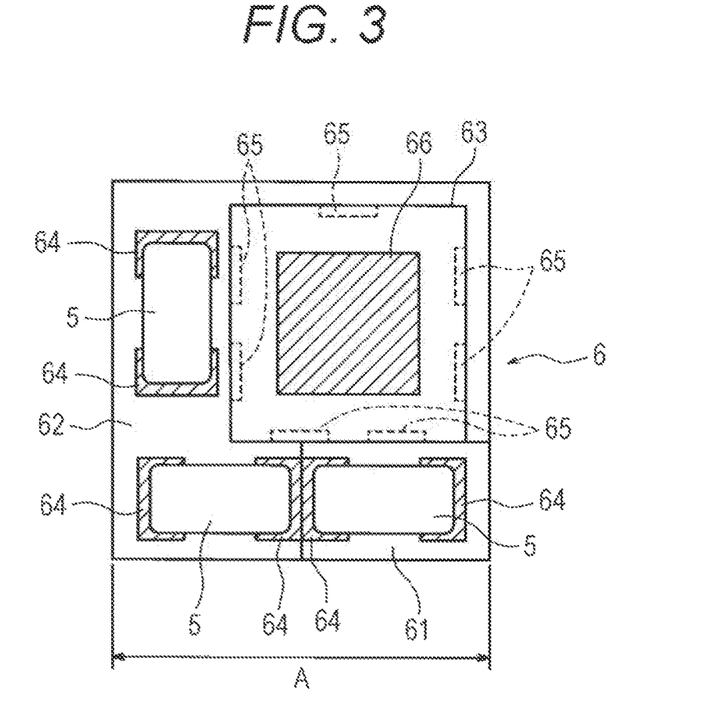
FIG. 3 is a plan view illustrating a mounting mode of a passive component.
Figure 4:
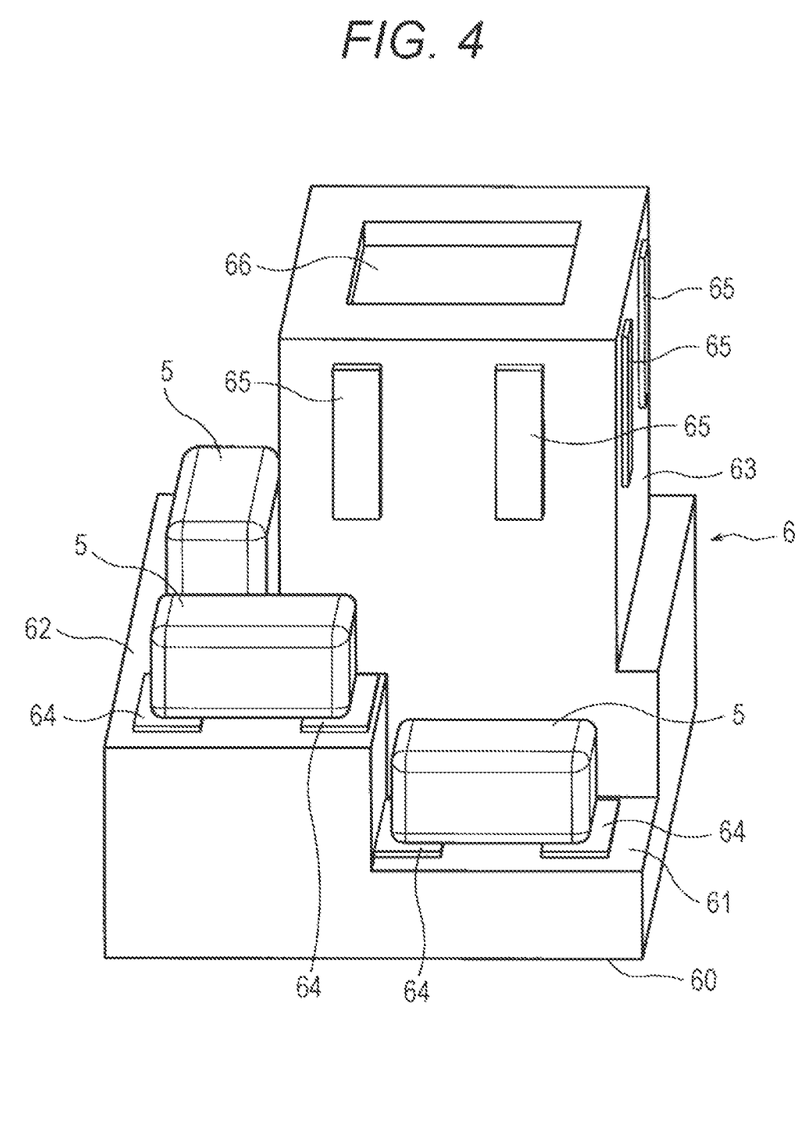
FIG. 4 is a perspective view illustrating the mounting mode of the passive component.

FIG. 3 is a plan view illustrating a mounting mode of the passive component 5, and FIG. 4 is a perspective view showing a mounting mode of the passive component 5. As illustrated, the mounting board 6 includes the second surface 61, the third surface 62, and a cable connection block 63 provided on the opposite side of the first surface 60.

The second surface 61 and the third surface 62 are mounting surfaces of the passive component 5 parallel to the first surface 60. As illustrated in FIGS. 3 and 4, the second surface 61 is formed to have a predetermined width from an edge along a half length of one side of the mounting board 6, and the third surface 62 is formed to have a width substantially equal to that of the second surface 61 along the remaining half length of the one side and the other side adjacent to the one side. As illustrated in FIGS. 2 and 4, the second surface 61 and the third surface 62 are continuous via a step that rises vertically from the second surface 61 at a center position of the one side.

A pair of connection lands 64 for connecting the passive component 5 is provided on the second surface 61. The connection land 64 is a rectangular conductive pattern extending in a width direction of the second surface 61. As illustrated in FIGS. 3 and 4, one connection land 64 is located along an edge of the second surface 61 with an appropriate clearance, and the other connection land 64 is located along a rising edge of the step without clearance. The passive component 5 is mounted to be bridged over the connection lands 64 and 64, and is connected by a solder reflow to be mounted.

Two pairs of connection lands 64 for mounting the passive component 5 are provided on the third surface 62. As illustrated in FIG. 3, the pair of connection lands 64 is provided in a portion continuous with the second surface 61 via a step, and one connection land 64 is located along a falling edge of the step without clearance and the other connection land 64 is located along an edge of the third surface 62 facing a falling edge with an appropriate clearance. As illustrated in FIG. 3, another pair of connection lands 64 is provided in the rest of the third surface 62, one connection land 64 is located along the edge of the third surface 62 with appropriate clearance, and the other connection land 64 is disposed to be spaced apart from one connection land 64 by a predetermined length. Two passive components 5 are mounted to be bridged over each pair of connection lands 64 and 64, and are connected by a solder reflow to be mounted. In FIG. 3, each connection land 64 is hatched, and thus, a positional relationship therebetween is clearly shown.

The cable connection block 63 is a columnar block that rises from the second surface 61 and the third surface 62 at an appropriate height, and has a rectangular cross section that occupies almost the entire surface except for the second surface 61 and the third surface 62 in the plane illustrated in FIG. 3. The cable connection land 65 is provided on four sides of the cable connection block 63, and a grounding land 66 is provided on an end surface of the cable connection block 63.

The cable connection land 65 is a rectangular conductive pattern extending in the height direction of the cable connection block 63, and as illustrated in FIG. 3, each of the two cable connection lands 65 is arranged side by side on three sides of the cable connection block 63, and one cable connection land 65 is provided on the remaining one side thereof. As illustrated by a two-dot chain line in FIG. 2, each of the plurality of core wires of the cable 17 described above is connected to each cable connection land 65.

The grounding land 66 is a rectangular conductive pattern provided in the center of the end surface, and an end portion of the shield provided in the cable 17 described above is connected to the grounding land 66 as illustrated by a two-dot chain line in FIG. 2. The cable connection land 65 and the grounding land 66 illustrated in FIGS. 2 and 3, respectively, are hatched.

Figure 5:
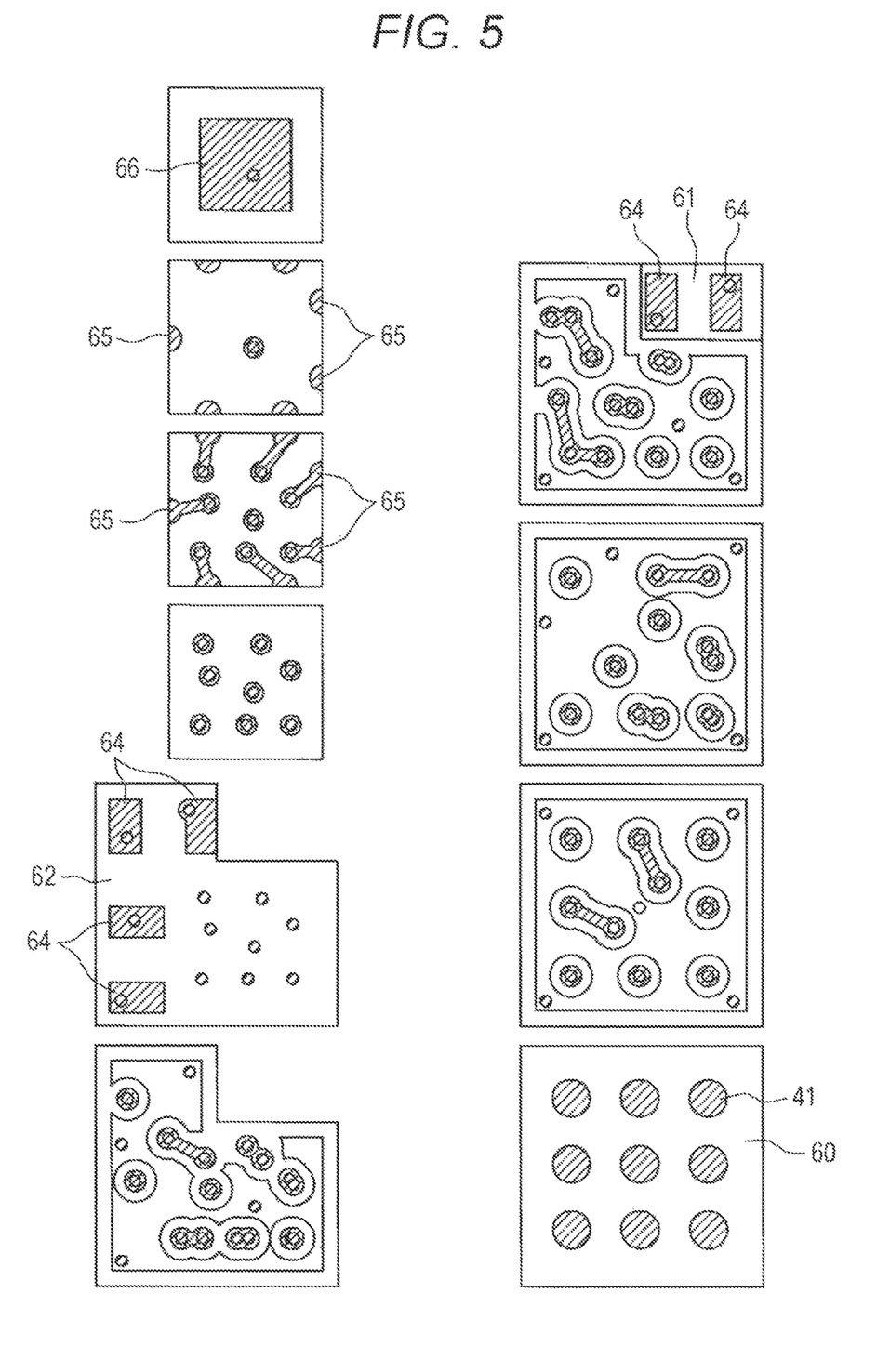
FIG. 5 is an explanatory diagram illustrating a mode of forming a conductive pattern and a via hole.

The mounting board 6 having the above configuration can be configured by, for example, stacking a plurality of ceramics boards in a thickness direction. The mounting board 6 illustrated in FIG. 2 is configured by stacking 12 ceramics boards, and the image sensor 4 surface-mounted on the first surface 60 is connected to the connection lands 64 provided on the second surface 61 and the third surface 62, and the cable connection land 65 provided on the cable connection block 63 by conductive patterns and via holes formed on each ceramics board. FIG. 5 is an explanatory diagram illustrating a mode of forming a conductive pattern and a via hole. In each figure, the conductive pattern is hatched, and the positions of the via holes penetrating each layer are indicated by a small circle.

The lower right of FIG. 5 illustrates a lower surface of the ceramics board of the lowermost layer in FIG. 2, that is, the first surface 60, and the lower surface is vertically and horizontally formed with the plurality of conductive patterns 41 corresponding to the plurality of electrodes 40 included in the image sensor 4. The remaining three figures on the right side of FIG. 5 illustrate upper surfaces of a ceramics board of a lowermost layer, a second layer, and a third layer in this order from the bottom. The second surface 61 provided with the pair of connection lands 64 and 64 is provided on a portion of the upper surface of the ceramics board of the third layer.

The six figures on the left side of FIG. 5 illustrate upper surfaces of a ceramics board of a fourth layer, a fifth layer, sixth and seventh layers, an eighth layer, ninth, tenth, and eleventh layers, and a twelfth layer in this order from the bottom. The third surface 62 provided with two pairs of connection lands 64 and 64 is provided on a portion of the upper surface of the ceramics board of the fifth layer. The ceramics boards of the sixth layer and subsequent layers constitute the cable connection block 63, and the cable connection land 65 is formed as a continuous conductive pattern on the side surface of the ceramics board of the eighth to eleventh layers, and is connected to an inner via hole by the conductive pattern provided on the ceramics board of the eighth layer. The grounding land 66 is provided on the upper surface of the ceramics board of the twelfth layer (uppermost layer).

In the imaging module 3 according to the first embodiment, the mounting board 6 in which the image sensor 4 is surface-mounted on the first surface 60 is provided with the second surface 61 and the third surface 62 which are located on the opposite side of the first surface 60 and provided with the connection lands 64 of the plurality of passive components 5, and the second surface 61 and the third surface 62 are continuous via the step. The connection lands 64 should be arranged so that a predetermined clearance can be maintained between the adjacent connection lands 64 in order to prevent a short circuit due to a solder bridge when the respective passive components 5 are connected.

Here, there is a step between the second surface 61 and the third surface 62, and this step functions as a three-dimensional clearance between the connection lands 64 provided on the second surface 61 and the third surface 62. Therefore, it is not necessary to secure a flat clearance between the connection land 64 provided on the second surface 61 and the connection land 64 adjacent to the connection land 64 and provided on the third surface 62, and as described above, it is possible to arrange the connection lands 64 along the step without clearance.

With such an arrangement, as illustrated in FIG. 3, the passive component 5 mounted on the second surface 61 and the passive component 5 mounted on the third surface 62 can be arranged adjacent to each other in a length direction in a plan view, and therefore, dimension A in FIG. 3 can be reduced by an amount corresponding to the clearance. The two passive components 5 on the third surface 62 are arranged so as to be orthogonal in the length direction, and it is easy to secure the clearance between the adjacent connection lands 64. It is possible to reduce the vertical and horizontal dimensions of the mounting board 6 and realize the mounting board 6 having a projected area equal to or smaller than that of the image sensor 4 in a cross section perpendicular to an axis.

When the imaging module 3 configured as described above is incorporated into the endoscope 1 as described above, only the minimum occupied area corresponding to the imaging surface of the image sensor 4 facing the objective lens 15 is required at the distal tip of the insertion tube 10, which makes it possible to meet the request to reduce the diameter of the insertion tube 10. The axial dimension of the mounting board 6 increases by the height of the step between the second surface 61 and the third surface 62, but the increase amount is small and the operation of changing the direction of the distal tip is not hindered.

Further, the imaging module 3 includes the columnar cable connection block 63, and the plurality of cable connection lands 65 are provided on the side surface of the cable connection block 63. As illustrated in FIG. 2, the connection of the cable 17 to the imaging module 3 can be easily and more reliably realized by a procedure of drawing a plurality of core wires, such as control lines and signal lines, from the end portion of the cable 17 that is approximately coaxially opposed to the cable connection block 63, and connecting each core wire to each of the corresponding cable connection lands 65.

The grounding land 66 is provided on the end surface of the cable connection block 63. The shield provided in the cable 17 can be easily grounded by connecting to the grounding land 66, and the influence of electromagnetic noise and electrostatic noise can be excluded.

Second Embodiment

Figure 6:
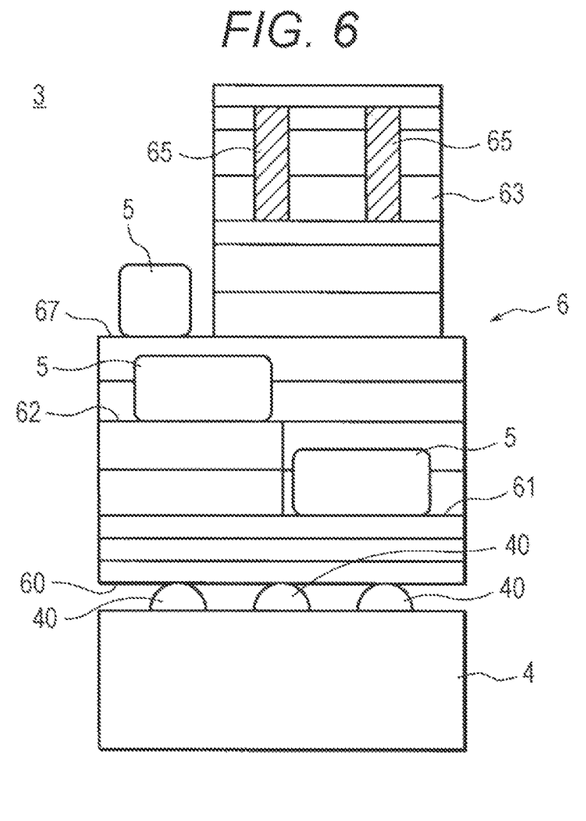
FIG. 6 is a side view of an imaging module according to a second embodiment.
Figure 7:
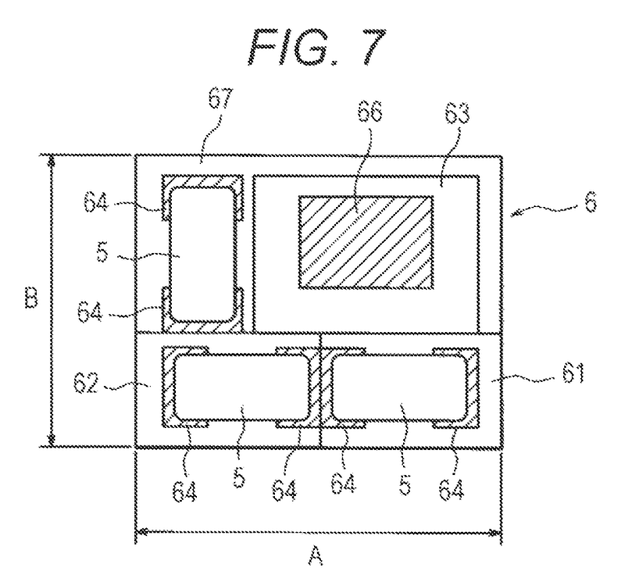
FIG. 7 is a plan view illustrating a mounting mode of a passive component.

FIG. 6 is a side view of an imaging module 3 according to a second embodiment, and FIG. 7 is a plan view illustrating a mounting mode of a passive component 5. In the imaging module 3 of the second embodiment, a mounting board 6 includes a second surface 61, a third surface 62, and a cable connection block 63 that are located on an opposite side of a first surface 60 on which an image sensor 4 is surface-mounted, as in the first embodiment, and further includes a fourth surface 67.

The second surface 61, the third surface 62, and the fourth surface 67 are mounting surfaces of the passive component 5 parallel to the first surface 60. As in the first embodiment, the second surface 61 is formed along a half length of one side of the mounting board 6, the third surface 62 is formed along the remaining half length of the one side, and the second surface 61 and the third surface 62 are continuous via a step that rises vertically from the second surface 61. The fourth surface 67 is formed along the other side adjacent to the one side, and the third surface 62 and the fourth surface 67 are continuous via a step rising vertically from the third surface 62.

Each pair of connection lands 64 for connecting the passive components 5 is provided on the second surface 61, the third surface 62, and the fourth surface 67, and the passive components 5 are mounted to be bridged over each pair of connection lands 64 and 64 and connected by a solder reflow to be mounted. In the second surface 61 and the third surface 62, the connection lands 64 located on the side of the step is arranged between the steps without a clearance as in the first embodiment. Even in the fourth surface 67, the connection land 64 located on the step side is located along a falling edge of the step without clearance.

In the imaging module 3 according to the second embodiment, one connection land 64 provided on the fourth surface 67 can be arranged along the falling edge of the step without clearance, and as in the first embodiment, in addition to being able to reduce dimension A in FIG. 7, dimension B in FIG. 7 can be reduced by an amount corresponding to the clearance. Accordingly, it is possible to further reduce the vertical and horizontal dimension of the mounting board 6 and realize the mounting board 6 having a projected area equal to or smaller than that of the image sensor 4 in a cross section perpendicular to an axis.

In the second embodiment described above, the third surface 62 and the fourth surface 67 may be configured to be continuous via the step rising from the third surface 62, but may be configured to be continuous via the step falling from the third surface 62.

The other configuration of the imaging module 3 according to the second embodiment illustrated in FIGS. 6 and 7 is the same as that of the imaging module 3 according to the first embodiment illustrated in FIGS. 2 and 3, and the corresponding components are designated by the same reference numerals as those in the first embodiment, and the description thereof will be omitted.

Note that the embodiments disclosed this time should be considered to be exemplary in all respects without being limited. The scope of the present invention is indicated by the scope of claims, not the above-mentioned significance, and is intended to include all modifications within the significance and scope equivalent to the claims.

REFERENCE SIGNS LIST

1 Endoscope
3 Imaging module
4 Image sensor
5 Passive component
6 Mounting board
10 Insertion tube
17 Cable
60 First surface
61 Second surface
62 Third surface
63 Cable connection block
64 Connection land
65 Cable connection land
66 Grounding land
67 Fourth surface

The invention claimed is:

1. An imaging module, comprising:
an image sensor; and
a mounting board on which the image sensor is mounted together with a plurality of passive components, the mounting board comprising a plurality of ceramics boards directly stacked atop one another in a thickness direction of the mounting board, each ceramics board of the plurality of ceramics boards having a different outer shape from other ceramics boards of the plurality of ceramics boards,
wherein a mounting part of the image sensor and a mounting part of a passive component of the plurality of passive components are located on opposite sides of the mounting board, and the mounting part of the passive component of the plurality of passive components is provided with a plurality of mounting surfaces that are continuous with each other via a step and are each provided with a connection land of the passive component of the plurality of passive components.

2. The imaging module according to claim 1, wherein the mounting board has a projected area equal to or smaller than that of the image sensor in a cross section perpendicular to an axis.

3. An imaging module, comprising:
an image sensor; and
a mounting board on which the image sensor is mounted together with a plurality of passive components, the mounting board comprising a plurality of ceramics boards directly stacked atop one another in a thickness direction of the mounting board, each ceramics board of the plurality of ceramics boards having a different outer shape from other ceramics boards of the plurality of ceramics boards,
wherein the mounting board includes:
a first surface on which the image sensor is surface-mounted;
a second surface that is located on an opposite side to the first surface and is provided with a connection land of a passive component of the plurality of passive components;
a third surface that is continuous with the second surface via a step and is provided with the connection land of the passive component of the plurality of passive components; and
a columnar cable connection block that rises from the second and third surfaces and to which a cable is connected.

4. The imaging module according to claim 3, wherein the mounting board further includes a fourth surface which is continuous with the second and third surfaces via a step and is provided with the connection land of the passive component of the plurality of passive components.

5. The imaging module according to claim 3, wherein cable connection lands for connecting a plurality of core wires of the cable are arranged side by side on a side surface of the cable connection block.

6. The imaging module according to claim 3, wherein the cable is shielded by a shield, and a grounding land for grounding the shield is provided on an end surface of the cable connection block.

7. An endoscope, comprising:
an imaging module incorporated in a distal tip of an insertion tube,
wherein the imaging module includes:
an image sensor; and
a mounting board on which the image sensor is mounted together with a plurality of passive components, the mounting board comprising a plurality of ceramics boards directly stacked atop one another in a thickness direction of the mounting board, each ceramics board of the plurality of ceramics boards having a different outer shape from other ceramics boards of the plurality of ceramics boards, and
the mounting board includes:
a first surface on which the image sensor is surface-mounted;
a second surface that is located on an opposite side to the first surface and is provided with a connection land of a passive component of the plurality of passive components;
a third surface that is continuous with the second surface via a step and is provided with the connection land of the passive component of the plurality of passive components; and
a columnar cable connection block that rises from the second and third surfaces and to which a cable is connected.

* * * * *